United States Patent [19]

Hagen et al.

[11] Patent Number: 4,873,974

[45] Date of Patent: Oct. 17, 1989

[54] NEUTRAL ELECTRODE FOR A HIGH-FREQUENCY SURGICAL INSTRUMENT

[75] Inventors: Uwe Hagen, Forchheim; Udo Redler, Effeltrich, both of Fed. Rep. of Germany

[73] Assignee: Siemens Aktiengesellschaft, Berlin and Munich, Fed. Rep. of Germany

[21] Appl. No.: 184,461

[22] Filed: Apr. 21, 1988

[30] Foreign Application Priority Data

Sep. 11, 1987 [DE] Fed. Rep. of Germany ....... 3730604

[51] Int. Cl.$^4$ ............................................. A61B 17/39
[52] U.S. Cl. ................................................ 128/303.13
[58] Field of Search ................... 128/303.13, 639–641, 128/644, 798, 802, 803

[56] References Cited

U.S. PATENT DOCUMENTS

| 3,534,727 | 10/1970 | Roman | 128/644 |
| 4,082,087 | 4/1978 | Howson | 128/640 |

FOREIGN PATENT DOCUMENTS

| 1219642 | 3/1987 | Canada . | |
| 0029245 | 11/1980 | European Pat. Off. | 128/798 |
| 394385 | 4/1924 | Fed. Rep. of Germany | 128/798 |
| 2849422 | 5/1979 | Fed. Rep. of Germany . | |
| 8205363 | 8/1985 | Fed. Rep. of Germany . | |
| 3544443 | 6/1987 | Fed. Rep. of Germany . | |
| 1333573 | 10/1973 | United Kingdom . | |
| 1441622 | 7/1976 | United Kingdom | 128/639 |

Primary Examiner—Lee S. Cohen
Attorney, Agent, or Firm—Lawrence C. Edelman

[57] ABSTRACT

A neutral electrode for a high-frequency electrosurgical instrument comprises three partial electrodes arranged in a predetermined direction on an insulated carrier. The carrier has on one side which is parallel to the predetermined direction, an electrical line terminal. The terminal contains electrical lines leading to the partial electrodes. In accordance with the invention, the surface area of the partial electrodes decreases in the predetermined direction. The electrode is applied on the patient so that the predetermined direction points toward the site of the surgical procedure. In this way, the partial electrodes are essentially acted upon by identical fractions of high-frequency energy, so that reliable monitoring of the contact between the partial electrodes and the patient is possible.

4 Claims, 1 Drawing Sheet

NEUTRAL ELECTRODE FOR A HIGH-FREQUENCY SURGICAL INSTRUMENT

BACKGROUND OF THE INVENTION

1. Field of the Invention

The invention relates to a neutral electrode for a High-Frequency (HF) surgical instrument.

2. Background of the Invention

A neutral electrode of the kind mentioned above, which operates with two planar partial electrodes, is known, for example, from German utility model No. 82 05 363. In this type of neutral electrode, monitoring of the electrically conducting connection with the patient is carried out by a control circuit having a low frequency control current. The control current flows from the contact surface of one partial electrode, through the skin of the patient, to the contact surface of another partial electrode. A similar two-part neutral electrode is known from German patent publication No. DE-A-28 49 422.

Consequently, multi-part electrodes permit determining with greater certainty whether the particular neutral electrode of the HF surgical instrument is in contact with the patient over a sufficiently large area or not. A monitor or safety circuit with which the contact of a three-part neutral electrode in the field of HF surgery can be monitored is known, for example, from FIG. 4 of U.S. patent application Ser. No. 929,561, filed Nov. 10, 1986.

A problem in constructing a multi-part electrode deals with finding a configuration which largely avoids a possible nonsymmetrical distribution of the high frequency energy emitted by the active electrode to the partial electrodes of the neutral electrode.

By using a two-part electrode, spurious measurements during the process of monitoring can occur. This can be of particular significance if the neutral electrode is fastened on an extremity of a patient, such as an arm or a leg. In particular, nonsymmetrical distribution of the high frequency energy being emitted by the active electrode over the partial electrodes of the neutral electrode can be brought about, which should be avoided.

Hence, it is an object of the invention to develop an electrode of the above mentioned kind in such a way, that uniform distribution of the high-frequency energy over its partial electrodes is ensured, in particular even when the electrode is applied on an extremity of the patient.

SUMMARY OF THE INVENTION

In accordance with the principles of the present invention, this object is solved by providing a neutral electrode for a high-frequency surgical instrument which comprises at least three partial electrodes arranged in a predetermined direction next to each other on a carrier. The partial electrodes have surface areas which are increasingly smaller in the predetermined direction. A side of the carrier which is essentially parallel to the predetermined direction includes an electrical line terminal to which electrical connection lines lead from the partial electrodes. Such electrode can be applied on the patient so that each of the partial electrodes receive practically an identical fraction of the high-frequency energy originating from the surgical field.

The electrode is applied on a patient in such a way that the predetermined direction points essentially toward the surgical field. In this manner, the differently sized surfaces of the partial electrodes are acted upon by approximately the same fraction of HF energy, given suitable dimensioning.

Other features and advantages of the invention will be apparent from the description of the preferred embodiments, and from the claims.

For a fuller understanding of the present invention, reference should now be made to the following detailed description of the preferred embodiments of the invention and to the accompanying drawings.

DETAILED DESCRIPTION OF THE PREFERRED EMBODIMENT

Figure 1:
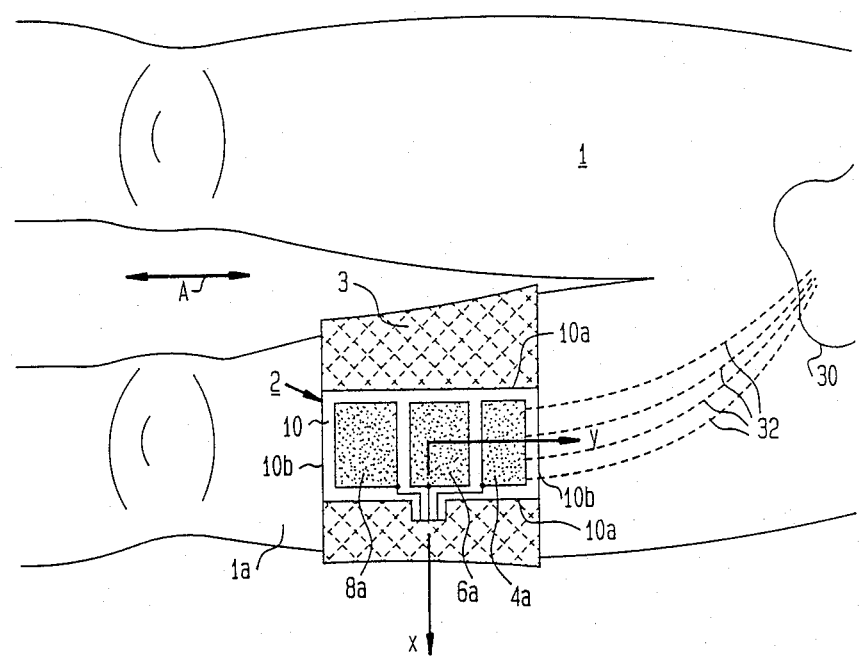
FIG. 1 illustrates the thigh of a patient to which a three-part neutral electrode constructed according to the principles of the invention is fastened.
Figure 2:
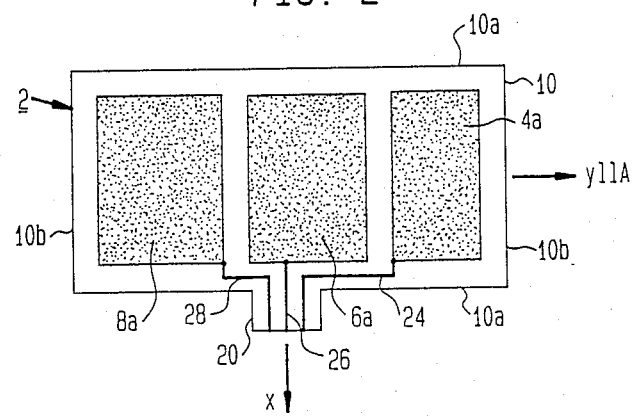
FIG. 2 illustrates a neutral electrode with three partial electrodes of different sizes according to FIG. 1.

In FIGS. 1 and 2, the x,y system of coordinates refers in each instance to the body axis A of a patient 1. The y axis is parallel to body axis A.

According to FIG. 1, a neutral electrode 2 is fastened to the thigh 1a of patient 1 with a tape 3 or by an self-adhesive device. Note, however, for purposes of clarity, neutral electrode 2 is shown from the underside. Neutral electrode 2 comprises three planar partial electrodes 4a, 6a, and 8a, of which each two are separated from each other by an insulating strip or strips of low electrical conductivity. The three partial electrodes 4a, 6a, and 8a are arranged next to each other in a predetermined direction y. They consist of a metal foil or of a metal mesh and are fastened on a flexible carrier 10. Carrier 10, which by itself or together with the entire electrode can be self-adhesive, it is essentially rectangular, longer in the predetermined y direction than in the perpendicular x direction, and projects at its outer edges beyond edges of partial electrodes 4a, 6a and 8a. It has two sides 10b which are shorter than two sides 10a which are parallel to the y direction. Carrier 10 consists, for example, of rubber which provides the forenoted strips of low electrical conductivity.

Carrier 10 has at its one side 10a an electrical line terminal 20. Line terminal 20 contains three connection lines 24, 26, and 28 arranged parallal for partial electrodes 4a, 6a and 8a, respectively. Feed lines 24 and 28 for partial electrodes 4a and 8a, respectively, are led on the carrier 10 adjacent to long side 10a. The terminal points of each of lines 24, 26 and 28 lies on a line parallel to the y axis. Two connection lines 24 and 28 are of identical length, which simplifies the manufacture of electrode 2 and keeps the storage cost low. Electrical line terminal 20 can be designed to a tab, and specifically in such a way that a multipole clamp can be connected to it, for example, using a crocodile clip.

In FIG. 1 the surgical field in patient 1 is designated by 30. It is here that the active electrode (not shown) operates during cutting or coagulation. Due to the arrangement of electrode 2 wherein the given direction x is transverse to surgical area 30 and also transverse to the body axis A, ensurance is given that the HF output originating from surgical area 30 is at least mostly uniformly distributed over partial electrodes 4a, 6a and 8a. The HF energy transferred to neutral electrode 2 is indicated by dashed lines 32.

FIG. 2 illustrates the same electrode as in FIG. 1, in which the predetermined direction is the y axis, which is again parallel to body axis A of patient 1. Neutral electrode 2 is applied on patient 1 in such a way that its y axis is parallel to body axis A. Partial electrodes 4a, 6a and 8a are aligned along the y axis. As clearly shown, the surface areas of partial electrodes 4a, 6a and 8a are not identical, although they are of identical width. Instead, partial electrodes 4a, 6a and 8a have surface areas becoming decreasingly smaller in the predetermined y direction. Thus, with the illustrated orientation of neutral electrode 2 to surgical field 30 (not shown), there is ensurance that discrete partial electrodes 4a, 6a and 8a are essentially acted upon by the same high frequency fraction of energy so that reliable proof regarding the contact of electrode 2 on patient 1 is ensured with a monitor circuit (not shown) of the type previously noted.

Thus, there has been shown and described novel apparatus for constructing a neutral electrode for a HF surgical instrument which fulfills all the objects and advantages sought therefore. Many changes, modifications, variations and other uses and applications of the subject invention will, however, become apparent to those skilled in the art after considering this specification and the accompanying drawings which disclose a preferred embodiment thereof. All such changes, modifications, variations and other uses and applications which do not depart from the spirit and scope of the invention are deemed to be covered by the invention which is limited only by the claims which follow.

What we claim is:

1. A neutral electrode assembly for a high-frequency surgical instrument, comprising:
    an electrode carrier; and
    at least three partial electrodes arranged in a predetermined direction next to each other on said electrode carrier so that the partial electrodes have surface areas which are decreasingly smaller in the predetermined direction, and the electrode carrier has on one side which is essentially parallel to the predetermined direction an electrical line terminal to which electrical connection lines lead from the partial electrodes.

2. An electrode assembly according to claim 1, wherein:
    said electrode carrier is longer in the predetermined direction than in a direction perpendicular to said predetermined direction and said partial electrodes form an essentially rectangular overall contact surface area having long sides in the predetermined direction and short sides in the perpendicular direction, said long sides being shorter than the sides of said carrier in said predetermined direction.

3. An electrode assembly according to claim 1, wherein:
    said partial electrodes form an essentially rectangular overall contact surface having two parallel short sides and two parallel long sides and said electrical line terminal is provided on one of said two long sides.

4. An electrode assembly according to claim 1, wherein:
    said electrical line terminal comprises a generally rectangular tab extending from one side of said electrode carrier, said tab having said electrical connection lines running parallel thereon and terminating along an edge thereof so as to be positioned for tapping via application of a multipole clamp to said tap.

* * * * *